United States Patent [19]

Scheinberg

[11] 4,049,673

[45] Sept. 20, 1977

[54] PREPARATION OF FERROUS HEMOGLOBIN AND ENZYMATIC DIGESTION PRODUCTS THEREOF ACTIVE FOR ABSORPTION OF CARBON MONOXIDE

[76] Inventor: Israel Herbert Scheinberg, 5447 Palisade Ave., Bronx, N.Y. 10471

[21] Appl. No.: 292,011

[22] Filed: Sept. 25, 1972

Related U.S. Application Data

[63] Continuation-in-part of Ser. No. 151,153, June 8, 1971, abandoned, and Ser. No. 102,869, Dec. 30, 1970, Pat. No. 3,693,327, which is a continuation-in-part of Ser. No. 85,057, Oct. 29, 1970, abandoned.

[51] Int. Cl.² ............................................. C09B 47/00
[52] U.S. Cl. ..................................... 260/314; 55/274; 424/101
[58] Field of Search .................... 260/314; 424/101

[56] References Cited

U.S. PATENT DOCUMENTS

| | | | |
|---|---|---|---|
| 2,466,710 | 4/1949 | Keil et al. | 260/314 |
| 3,756,582 | 9/1973 | Scheinberg | 55/274 |
| 3,998,946 | 12/1976 | Condie et al. | 424/101 |

Primary Examiner—Alan L. Rotman
Attorney, Agent, or Firm—Blum, Moscovitz, Friedman & Kaplan

[57] ABSTRACT

Ferrous hemoglobin in a form suitable for absorption of carbon monoxide is produced from a hemoglobin solution, buffered to prevent denaturation of the hemoglobin, and containing an effective reductant. The quantity of reductant present is at least sufficient to counteract the effect of oxygen in such air as comes in contact with the hemoglobin. Enzymatic digestion products of hemoglobin, also active for the absorption of carbon monoxide are produced by controlled decomposition of hemoglobin. These products are lower in equivalent weight than is hemoglobin so that the quantity needed for absorbing a given quantity of carbon monoxide is reduced.

21 Claims, No Drawings

PREPARATION OF FERROUS HEMOGLOBIN AND ENZYMATIC DIGESTION PRODUCTS THEREOF ACTIVE FOR ABSORPTION OF CARBON MONOXIDE

CROSS REFERENCE TO RELATED APPLICATIONS

This application is a continuation-in-part application of my co-pending application Ser. No. 151,153 filed June 8, 1971 now abandoned and of my co-pending application Ser. No. 102,869 filed Dec. 30, 1970 now U.S. Pat. No. 3,693,327, itself a continuation-in-part application of then co-pending application Ser. No. 85,057 filed Oct. 29, 1970. Application Ser. No. 85,057 has been abandoned.

BACKGROUND OF THE INVENTION

As is well-known, carbon monoxide (CO) is a toxic, odorless, colorless gas capable of producing discomfort, illness, mental and physical disability and/or death if present in inhaled air, gas or smoke in sufficiently high concentrations. Combustion of many kinds such as occurs in coal and oil fires, gas flames, internal combustion engines, and burning tobacco, in particular, are common sources of CO. Marshes also generate CO.

Even non-smokers are frequently exposed to potentially excessive quantities of carbon monoxide since carbon monoxide is a substantial air pollutant produced by automobiles, internal and external combustion engines, in many industrial processes, and by neighboring smokers. Thus, guards and workers in automobile tunnels, or passengers in automobiles may be exposed to excessive quantities of carbon monoxide.

As an illustration of the danger presented by carbon monoxide in air, studies have shown that where the product of hours of exposure and parts of carbon monoxide per 10,000 parts of air equal 15, a danger to life is present. It therefore would be highly desirable that effective means be found for absorbing carbon monoxide either at the point where generated or from air to be inhaled by individuals.

Hemoglobin, the term as used herein designating ferrous hemoglobin or oxyhemoglobin, is an attractive possibility for use toward such ends but has not been available due to the fact that when it is no longer within the erothrocyte and is exposed to oxygen of the air it forms methemoglobin which is inactive toward carbon monoxide. Further, the equivalent weight of hemoglobin is high, making it necessary that relatively large quantities of the material be used for absorption of carbon monoxide. The molecular weight of hemoglobin is about 66,000 and each hemoglobin molecule contains four iron atoms, active in absorbing carbon monoxide, so that the equivalent weight of hemoglobin relative to absorption of carbon monoxide is about 16,500. In contrast, the molecular weight of each heme moiety which contains an atom of iron is approximately 600. Since it is this portion of the hemoglobin molecule which is responsible for the absorption of carbon monoxide by the formation of a stable complex, it would obviously be desirable to eliminate, in so far as is possible, those portions of the hemoglobin molecule which are inactive with respect to absorption of carbon monoxide.

SUMMARY OF THE INVENTION

Blood collected, preferably, from large animals is mixed with a suitable anti-coagulant or is defibrinated. The resultant material is centrifuged to separate off the erythrocytes, i.e., red cells. The red cells are washed with a sodium chloride solution and lysed by standard methods. The red cell ghosts are centrifuged off and the supernatant hemoglobin solution is buffered within a range such that denaturation does not occur. An effective reductant is added in a quantity essentially sufficient to prevent the formation of methemoglobin by oxygen in the limited quantity of air to which the solution will be exposed during processing. Further reductant may be added to prevent formation of methemoglobin from ferrous hemoglobin by oxygen in the air to which the hemoglobin will subsequently be exposed. The hemoglobin may be prepared in amorphous form by freeze-drying, using conventional techniques, by spray-drying, drum drying, or by drying in proximity to a desiccant in an enclosure, preferably in vacuo, or under an inert gas.

Any of the above drying procedures results in a product which contains both hemoglobin and protective reductant. However, where crystalline hemoglobin is desired, this may be produced by adding ammonium sulfate or chilled ethanol to the solution and inducing crystallization by dropping the temperature.

Enzymatic digestion products of hemoglobin having a lower equivalent weight with respect to the absorption of carbon monoxide than does hemoglobin itself are produced by treating hemoglobin in solution with a protease. The solution is buffered to about 7.5 and contains excess reductant based on the number of equivalents of ferrous iron present. A reduction in equivalent weight by a factor of about three is achieved by dialyzing off the inactive portions of the hemoglobin removed by the protease.

Accordingly, an object of the present invention is ferrous hemoglobin in solid state.

Another object of the present invention is ferrous hemoglobin in a form suitable for use as a filter intended for absorption of carbon monoxide.

A further object of the invention is crystalline ferrous hemoglobin.

Still another object of the invention is solid ferrous hemoglobin in combination with an effective reductant.

A particular object of the present invention is a composition containing hemoglobin or enzymatic digestion products thereof, in combination with a reductant, said composition being effective for the absorption of carbon monoxide.

A significant object of the present invention is to provide methods of preparation of crystalline and amorphous hemoglobin.

An important object of the present invention is to provide a method for preparing enzymatic digestion products of hemoglobin effective for the absorption of carbon monoxide and having a lower equivalent weight than that of hemoglobin with respect to said absorption.

Still other objects and advantages of the invention will in part be obvious and will in part be apparent from the specification.

The invention accordingly comprises the several steps and the relation of one or more of such steps with respect to each of the others, and the compositions possessing the features, properties, and the relation of constituents, which are exemplified in the following detailed disclosure, and the scope of the invention will be indicated in the claims.

DESCRIPTION OF THE PREFERRED EMBODIMENTS

In preparation for the process of producing ferrous hemoglobin or lower equivalent weight enzymatic digestion products thereof, blood is collected from cows, horses, sheep, pigs, humans or other living creatures using hemoglobin for the transport of oxygen. The blood is collected in a suitable anti-coagulant such as, but not limited to, sodium citrate, sodium oxalate, sodium ethylenediaminetetraacetate, or, the blood may be defibrinated on collection.

The blood, whether defibrinated or in anti-coagulant is centrifuged to obtain the red cells. These are washed with a sodium chloride solution by centrifugation. Preferably the washing is carried out three times. The cells are then lysed by such standard methods as repeated freezing and thawing, or by suspension in distilled water with or without addition of an organic solvent such as diethyl ether. The red cell ghosts which result from the lysing are centrifuged off and the supernatant hemoglobin solution is brought to a pH between about 6.0 and about 8.5, using a suitable buffer. If the pH is allowed to go outside this range, denaturation of the hemoglobin may occur. A suitable buffer is prepared from $NaH_2PO_4$ and $Na_2HPO_4$ in proportions appropriate to the desired pH range. The concentration of sodium phosphate buffer should be in the range of 0.5–1.0 molar for a solution containing about 5–10% hemoglobin. Another buffer which is suitable is tris (hydroxymethyl aminoethane-HCl). This buffer, known as Tris-HCl buffer is effective in producing a pH of about 7.5.

In general, it is desirable to minimize the contact of the solution with air during processing steps. This is done by carrying out steps of the process as rapidly as possible and by working at reduced pressure or blanketing with an inert gas where possible. However, some contact with air is inevitable and it is this contact with air which has hitherto been the cause of the conversion of extra-erythrocyte ferrous hemoglobin to methemoglobin in which the iron atoms are in the ferric state. This difficulty is eliminated in accordance with the present invention by adding a reductant effective for preventing formation of methemoglobin from ferrous hemoglobin. Examples of effective reductants are ascorbic acid, sodium dithionite, the formula for which is $Na_2S_2O_4$, and methylene white which is the reduced form of methylene blue. In sodium dithionite, it is, of course, the dithionite ion which is the reductant.

The quantity of reductant needed for this purpose depends, of course, on the degree to which the solution is exposed to air. In general, it has been found, one to five equivalents of reductant per equivalent of iron atoms in the hemoglobin or hemoglobin derivative are sufficient. If contact with air is sufficiently minimized, then even less than 1 equivalent of reductant per equivalent of iron atoms will be adequate. It should be noted that where the ferrous hemoglobin or digestion products thereof produced in accordance with the invention are to be exposed to oxygen during use or further processing, as where said hemoglobin or digestion products thereof are to be used in a device for the removal of CO from an air stream, then even larger ratios of reductant to iron may advantageously be used. The actual quantity of reductant incorporated with such hemoglobin or digestion products thereof would be such as to prevent oxidation of the hemoglobin or its derivatives to methemoglobin or analogues thereof by the quantity of oxygen to which it is expected that the hemoglobin or digestion products will be exposed during the course of said processing or use. The additional reductant above that necessary in the production of hemoglobin or digestion products thereof in accordance with the present invention may be added to the solutions thereof during said production or combined with the hemoglobin or digestion products subsequent to production. For example, a specific application for hemoglobin produced in accordance with the present invention, would be use in a filter device for removal of CO from cigarette smoke before inhalation. The amount of reductant associated with hemoglobin or derivatives in such a device should be substantially sufficient to prevent oxidation of said hemoglobin or derivatives by the oxygen in said cigarette smoke and elsewhere to which the hemoglobin or derivatives would normally be exposed. As a practical matter consideration of weight and volume would limit the quantity of reductant actually utilized.

Significantly, the reductant added functions analogously to an enzyme, methemoglobin reductase present in red blood cells. Although almost all of the hemoglobin in blood reacts with the oxygen which diffuses into erythrocytes in the pulmonary alveoli to form oxyhemoglobin, a very small proportion of such hemoglobin is continually being oxidized to methemoglobin which is inactive in transporting oxygen. The methemoglobin is reconverted to hemoglobin by methemoglobin reductase; the reductant added during or after the processes described herein performs the same function in reducing the small amount of extra-erythrocytic hemoglobin being so continually oxidized to methemoglobin by contact with air.

As a result of this phenomenon the quantity of reductant need not be stoichiometrically equivalent to or greater than the quantity of oxygen to which the ferrous iron will be exposed. However, as aforenoted, it has been found preferable to use from one to five equivalents of reductant per equivalent of ferrous iron present.

Where the reductant is acidic in nature as is the case with ascorbic acid, the pH of the solution may drop toward the previously specified lower limit as the reductant is added. In such a case, it is desirable to maintain the pH within the specified limits by addition of a further quantity of buffer either concurrently with addition of the acid, or periodically. Also, it is possible to dissolve the reductant in a concentrated solution of the buffer and then add the solution containing both components to the hemoglobin solution. In keeping with the need to avoid pH below about 6.0 or above about 8.5, it is desirable that the buffer and the reductant be added under conditions such that high local concentrations of reductant or buffer are avoided. The buffer is added, preferably as a concentrated solution to avoid introduction of excessive amounts of water which would otherwise have to be removed during the drying process, and the solution is vigorously stirred as by introduction of the buffer solution through small jets. Similarly, the reductant if added separately, is also added as a solution through small jets with vigorous stirring of the main body of the solution. Alternatively, a conventional rotating stirrer may be used, provided the introduction of air into the solution is avoided.

Hemoglobin or its enzymatic digestion products in amorphous form is prepared by drying a solution containing hemoglobin or its enzymatic digestion products, buffer and reductant by conventional techniques already alluded to. As is obvious, the product also contains buffer and reductant. The same result can be achieved by drying, preferably in vacuo, over a drying agent. Examples of suitable drying agents are sulphuric acid, calcium chloride, silica gel, alumina and magnesium perchlorate.

Hemoglobin in crystalline form may be produced by making the solution 45 to 55% saturated with respect to ammonium sulfate. In the process of adding ammonium sulfate, the pH of the solution should be monitored to make certain that it does not drop below about 6.0. If necessary, more buffer should be added, and it is desirable that excess reductant also be present. The solution is then cooled to 0° C–10° C and preferably 0° C–4° C to crystallize out the hemoglobin. Alternatively, instead of ammonium sulfate, ethanol, preferably chilled to below 0° C, may be added in quantity such as to bring the final concentration to about 20%, and the solution is then allowed to stand at $-15°$ C to 0° C until crystallization is complete.

The product may be further purified by redissolving the crystals at a pH of 7.5–8.0 in the presence of reductant, bringing the solution to a pH of about 7.0 and allowing the solution to stand at between 0° C and 10° C and preferably between 0° C and 4° C until recrystallization is complete. This usually takes about 12 hours.

EXAMPLE 1

PRODUCTION OF HEMOGLOBIN

Bovine blood was collected in sodium citrate solution ("acid-citrate-dextrose") as anti-coagulant. The red cells contained therein were separated by centrifugation, and washed three times with 0.85% aqueous sodium chloride with centrifugation. One hundred sixty ml of packed red cells were lysed in 850 ml of distilled water and the red cell ghosts were removed by centrifugation, yielding 50 g of hemoglobin in 900 ml of solution. To this solution were added 100 ml of 1.0 molar sodium phosphate buffer (0.8 mole fraction $Na_2HPO_4$ and 0.2 mole fraction $NaH_2PO_4$) through a small jet. The sultant solution had a pH of 7.5.

The solution was chilled to 0° C and 1.87 g of ascorbic acid, dissolved in 20 ml of 0.5 molar phosphate buffer, pH 7.5 was added to the buffered solution with vigorous stirring to avoid local concentration excesses. At this stage virtually all of the hemoglobin was in the reduced or ferrous state, as indicated by spectrophotometric examination of a sample.

The solution was then freeze-dried producing a powder in which 65% of the protein present was in the form of ferrous hemoglobin. This hemoglobin was active in the absorption of CO from a stream of air. The remainder of the powder consisted of methemoglobin, phosphate salts and ascorbic acid. The analysis of the powder was carried out spectrophotometrically.

It shouid be noted that the effectiveness of the phosphate is not dependent on the particular cation used. Consequently, an equivalent amount of potassium phosphate buffer would serve as well. Also, as aforenoted, tris-HCl buffer may be used instead of phosphate buffer.

In the hemoglobin molecule only those portions of the molecule adjacent to the iron atoms are essential in maintaining its activity in absorbing CO. Since the hemoglobin molecule has a molecular weight of about 66,000 and contains four iron atoms, the equivalent weight for absorption of CO is about 16,500. It would be highly desirable to lower the equivalent weight for reaction with CO. This has been effected by an enzymatic digestion process followed by dialysis to remove inactive components split from the hemoglobin molecule as described in the following example.

EXAMPLE 2

ENZYMATIC DIGESTION PRODUCTS OF HEMOGLOBIN OF LOWER EQUIVALENT WEIGHT

Crude Hemoglobin

Red cells from bovine blood were washed three times with saline and lysed by dilution with four volumes of distilled water. The solution was centrifuged at 10,000 g for 10 minutes after which a clear solution of crude hemoglobin was aspirated. The solution was adjusted to 1.0% in hemoglobin ($E^{1\%}_{1\ cm,\ 577\ m\mu} = 18.0$) in Tris-HCl buffer having a pH of 7.5.

This solution has the characteristic optical absorption spectrum of oxyhemoglobin (free of methemoglobin) at 577 m$\mu$ ($E^{1\%}_{1\ cm,\ 577\ m\mu} = 8.90$) and at 542 m$\mu$ ($E^{1\%}_{1\ cm,\ 542\ m\mu} = 8.35$). The absorption at these two wavelengths indicated that approximately 90% of the hemoglobin was in the ferrous form.

To the solution was then added enough sodium dithionite to bring its concentration up to 0.004%. Dithionite is an effective reductant with respect to methemoglobin and at this concentration, is present in an excess of about 40% over the normality of ferrous iron present. For the solution as described, the quantity of sodium dithionite would be about 40 mg/l.

Digestion With Proteolytic Enzymes

The ferrous hemoglobin solution containing Tris-HCl buffer and reductant was incubated at room temperature in the presence of 1 mg per liter of Pronase (protease from Streptomyces griseus, from Sigma chemical Co., St. Louis, Missouri, Catalog No. P-5130) per ml of 1% hemoglobin solution. The change in optical absorption spectrum was monitored on aliquots of the solution diluted 1:10 with Tris-HCl buffer. 20 to 30% of the oxyhemoglobin peaks (577 and 542 m$\mu$) disappeared after 16 hours, indicating that about 75% of the original ferrous heme compound was still present.

Approximately 75% of the original weight of protein had become dialyzable by this digestion. When the dialyzable material was removed by dialysis, only 25% of the original weight remained. Consequently, as is evident, the average equivalent weight of each ferrous iron compound has been reduced better than three-fold, that is, from about 16,500 to about 5,000.

EXAMPLE 3

TRYPSIN

Crystalline trypsin (bovine) from C. F. Boehringer and Soehne, Mannheim, Germay was substituted for the Pronase of Example 2, and the procedure of Example 2 was followed. The result, namely, the extent of reduction of the equivalent weight for absorption of CO was approximately the same as that of Example 2.

The dialyzed material in solution can be obtained in dry form by freeze-drying, spray-drying, drum drying or drying by a desiccant, preferably in vacuo, processes which yields a mixture of digestion product, buffer and reductant. As with the process for obtaining hemoglobin, the digestion products can be crystallized from water which is properly buffered or from an ethanol-water solution by dropping the temperature of precipitate out the greater portion of the digestion products. The product achieved by either of these processes, i.e., drying or crystallization from solution is not pure. In the case of drying, the buffer and the reductant are mixed with the digestion products. In the case of crystallization, a mixture of enzymatic digestion products is obtained together with some buffer and reductant.

As is evident, the amount of reductant added in the process of obtaining hemoglobin digestion products can be varied, the quantity being selected to be appropriate to the amount of oxygen with which contact is anticipated. Where the material is to be used in a cigarette filter, for instance, there will be contact with a lower concentration of oxygen then will be true for a filter through which room air is passed. Where the quantity of reductant in combination with the CO absorbent is to be large, it is evident that the preferable method of converting the hemoglobin or digestion products to a solid is by drying since no loss of reductant takes place in such a process. Conversely, where either hemoglobin or hemoglobin digestion products are to be crystallized out, there is definitely fractionation. Nevertheless, for certain uses where hemoglobin is desired in pure form, crystallization and recrystallization, if desired, can be carried out from solution. As aforenoted, the preferable crystallization temperature for water solutions lies between 0° and 10° C and a temperature between 0° and 4° C is even better, ensuring a greater yield.

Methods by which amorphous or crystalline hemoglobin and amorphous or crystalline heme in combination with an effective reductant may be utilized for absorption of carbon monoxide are described, as aforenoted, in my co-pending application having the Ser. Number 102,869. The specification and drawings of said application are incorporated by reference herein as if fully set forth herein. The combination of hemoglobin or hemoglobin digestion products may be incorporated in a filter for interposition between tobacco in a cigarette, cigar or pipe and the smoker. In a cigarette, for instance, means may be provided for supporting said filter medium as by impregnating paper with a solution of the carbon monoxide-absorbing material, buffer and reductant, freeze-drying the product, shredding the paper and packing same into a space between two porous discs of paper proximate the end of a cigarette which is held in the smoker's mouth. The section of the cigarette in which the carbon monoxide absorbent is incorporated may include a window portion to permit visual examination of the filter medium. The window may be positioned in alignment, preferably, with that portion of the filter medium which is nearest the smoker.

In a test of the effectiveness of the enzymatic digestion product, filter material was prepared by saturating a light, absorbent paper (tea-bag tissue) with a solution of enzymatic digestion products and drying it. The resulting sheet contained 78% of solids exclusive of the paper. This sheeting was shredded with scissors and packed into a tube with an internal diameter of 19 mm. 7½ grams of the sheet material was used at a packing volume of 22 ml. Thus packed, this filter had a pressure drop, measured at the standard air flow rate use for testing cigarette filters, of two inches of water.

The filters were evaluated by attaching them to CAMEL cigarettes which were smoked by machine. The CO content of the combustion product was determined by gas chromatography and the tar delivery of the cigarette was determined simultaneously by glass fiber filter pads. The results of this test were as follows:

|  | CO | Tar |
|---|---|---|
| Test Cigarette | 4% | 4 mg |
| CAMEL | 5.5% | 22 mg |

The reduction of the CO content, is experimentally significant. It should be noted that no attempt was made in this experiment to maximize the content of carbon monoxide absorbent in the filter volume. Consequently, substantial increases in the efficacy of removal of carbon monoxide can be anticipated by improved design of the filter. Furthermore, there is not indication from the results obtained thus far that the lowering of the equivalent weight of carbon monoxide absorbent has reached a limit.

Other means of incorporating carbon monoxide absorbent in accordance with the present invention in a cigarette filter are also available. Thus, freeze-dried material can be compressed into pellets of a size such as to provide adequate surface area for the heterogeneous reaction between carbon monoxide and the carbon monoxide absorbent and yet permit free draw of smoke therethrough without excessive pressure drop. Alternatively, cellulose floc can be impregnated with absorbent (either hemoglobin or digestion products thereof), in combination with reductant.

Other methods of utilization of the carbon monoxide absorbent in accordance with the invention can be based on the use of paper or cloth impregnated with said absorbent which is fed from one roll to a second roll. The portion intermediate the two rolls can be drawn across the path of air in an air circulation system from which it is desired to absorb carbon monoxide. Such a system might be used in an automobile service station in which engines are operated as part of the process of repair. Under such circumstances the impregnated paper could be continuously fed as a means of keeping the carbon monoxide level within specified limits. The proper rate at which to move the paper from one roll to the other can be determined by measurement of infra-red absorption by the impregnated paper. Thus, at a wavelength of $0.8\mu$, hemoglobin and oxyhemoglobin exhibit an obsorption coefficient, $\epsilon$, of 0.2 while carboxyhemoglobin exhibits an $\epsilon$ of 0.018. This difference in absorption can be utilized to provide an indication of saturation of the filter medium according to the invention.

It should be noted that although the binding of carbon monoxide to hemoglobin is about 250 times as strong as that of oxygen, the binding is nevertheless reversible. Thus, it is possible to regenerate an exhausted filter by flushing it with air which is essentially free of carbon monoxide. When so flushed, the hemoglobin is again suitable for removing carbon monoxide from gases passed therethrough.

Although, hemoglobin and its digestion products in the presentation thus far have been viewed solely from the standpoint of absorption of carbon monoxide, a filter medium according to the present invention can be adapted to remove from a stream of air materials other than carbon monoxide as well. This point is important with respect to the filtration of constituents of cigarette smoke known to be harmful, such as tar as shown above. Thus, if hemoglobin is precipitated in amorphous or crystallized form from an acid solution, the alpha and epsilon amino or histidyl groups of the protein would be in the charged —N+— form. In such a form, the hemoglobin or digestion products thereof in the filter medium would absorb negatively charged organic volatiles such as acetic acid, formic acid and the like.

On the other hand, if the hemoglobin or digestion products are formed in an alkaline medium, the carboxyl groups of the protein would be present in a negatively charged form. This form of the filter medium according to the invention would absorb amines and other positively charged, or potentially positively charged, volatiles, such as ammonia, present in the gas passing through the filter medium. As is obvious, it would be possible to back a filter in a cigarette so that, say half the carbon monoxide absorption material would have been precipitated or crystallized from a low pH medium and the other half precipitated or crystalized from a high pH medium, thus providing for removal of both acidic and alkaline constituents in the cigarette smoke.

A further embodiment of the filter suitable for use with smoking products is a cigar or cigarette holder having a hollow tip portion adapted to receive a cigar or a cigarette and having an intermediate portion between the mouthpiece of the cigarette holder and the tip portion, in which is disposed a filter medium produced in accordance with the teachings of the present invention. It is convenient that the cigarette holder may be separated into two parts joinable by means of threads or a friction fit. By such means, access is readily provided to the chamber within which is to be placed a filter medium according to the present invention. A transparent window in the wall of the filter support makes it possible to detect by visual examination when the filter medium must be replaced. A similar construction can be utilized in pipes. The indication of exhaustion is a cherry red color.

The filter medium may also be formed in sheet or membrane form by permitting a solution of hemoglobin or its enzymatic digestion products to dry on a thin metal plate of the type utilized for drying glossy photograph prints. The resulting sheet or membrane of hemoglobin or its enzymatic digestion products can be coiled on a supply roll for continuous or intermittent advancement past a stream of air which may be produced by a blower. By the use of the infra-red characteristics of the filter medium as described above, saturation can be detected, preferably automatically, to determine the rate at which the filter medium must be advanced, whether continuously or intermittently. As indicated, advancement of the sheet can be effected automatically by suitable detection means coupled to suitable sheet-moving means. Furthermore, the detection means can be arranged to sound an alarm or activate a visible signal at saturation of a filter medium.

As aforenoted, the filter medium can be regenerated by directing a stream of essentially carbon monoxide-free air or oxygen against the filter medium during periods, such as at night, when the filter medium is not in use. Needless to say, the filter media of the present invention can be incorporated in felt-like materials used for removing dust, pollutants, pollens, etc.

Further, the detection means described above can be applied to detect an excess of carbon monoxide in the atmosphere of an enclosed space such as a room or the inside of a vehicle, without being coupled to a filtering arrangement. In such an embodiment a quantity of hemoglobin or its enzymatic digestion products is exposed to the atmosphere in a room or in the air stream of a heating, cooling or air circulating system, and positioned relative to a detection device such as a light source and a photocell for the detection of changes in color or infra-red absorption. The photocell is coupled to a suitable alarm for signaling the presence of a dangerous excess of carbon monoxide. For such an embodiment, a solution of hemoglobin or its enzymatic digestion products, as well as crystalline or amorphous hemoglobin or its solid enzymatic digestion products could be used, so long as the absorbent materials are in the present of a suitable quantity of a suitable reductant, such as methylene white, ascorbic acid or dithionite ion in the form of an alkali dithionite.

To establish whether the CO content of the air exceeds a specified limit, the time required for the composition to change color must be noted. This can be carried out by coupling a timer to the detection device. Alternatively, a paper impregnated with the composition may be passed between a supply roll and a takeup roll, where the feed rate is such that if the paper changes color before reaching the take-up roll then the CO content of the air exceeds the specified limit.

The above-described applications of the filter media and carbon monoxide detector in accordance with the invention are more particularly described in my co-pending application Ser. No. 102,289 filed Dec. 30, 1970, now U.S. Pat. No. 3,693,327, with the specification and drawing of said patent being incorporated herein by reference as if fully set forth in this application.

Although only three reductants have been disclosed, as is obvious, any material which is a sufficiently strong reducing agent to prevent the formation of methemoglobin from ferrous hemoglobin and which is nonvolatile may be used.

It will thus be seen that the objects set forth above, among those made apparent from the preceding description, are efficiently attained and, since certain changes may be made in carrying out the above process and in the composition set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. Method of producing ferrous hemoglobin from an aqueous solution of hemoglobin wherein said solution is to be exposed to a limited quantity of oxygen during production of said ferrous hemoglobin, comprising the steps of adding during agitation of said solution a buffer under conditions such as to maintain said solution at a pH between about 6.0 and 8.5 both locally and overall, and during addition of reductant and adding to said solution a quantity of an effective reductant sufficient to substantially prevent the inactivation of said hemoglobin for the absorption of CO by said limited quantity of oxygen.

2. Method as defined in claim 1, wherein said buffer is a phosphate buffer or a tris chydroxymethyl aminoethone 3. Method as defined in claim 1, wherein said reductant is selected from the group consisting of ascorbic acid, methylene white and dithionite ion.

4. Method as defined in claim 1, further comprising the step of adding buffer together with said reductant to bring the pH of said solution toward the center of the pH range of about 6.0 to 8.5.

5. Method as defined in claim 1, wherein the quantity of effective reductant added is substantially sufficient to prevent the inactivation of said hemoglobin for absorption of CO by oxygen to which it is expected that said hemoglobin will be exposed during and subsequent to production.

6. Method as defined in claim 1, wherein the ratio of effective reductant to the quantity of hemoglobin present, expressed in equivalents with respect to the ferrous iron content of said hemoglobin, is in the range of 1:1 to 5:1.

7. Method as defined in claim 1, further comprising the step of drying said solution by one of the processes, freeze-drying, drum-drying and spray-drying, and placing in proximity to a desiccant, thereby producing amorphous hemoglobin.

8. The process as defined in claim 1, further comprising the steps of adding a quantity of ammonium sulfate to said solution, monitoring the pH of said solution during addition of said ammonium sulfate and adding buffer as necessary to keep the pH from dropping below 6.0, the quantity of added ammonium sulfate being from 45% to 55% of that necessary to saturate said solution, chilling said solution to $-15°$ C to $0°$ C, allowing said solution to stand until crystallization of said ferrous hemoglobin is complete and separating off the crystals fomed.

9. The process as defined in claim 8, further comprising the steps of redissolving said crystals in a solution containing effective reductant and buffered to a pH between about 7.5 and 8.5, adjusting the pH to about 7.0 and cooling said solution to between $0°$ C and $10°$ C to crystallize out said hemoglobin in purified form.

10. The process as defined in claim 8, further comprising the steps of adding ice-cold ethanol in quantity which is about 25% of the weight of said solution, cooling said solution to between $-15°$ C to $0°$ C, allowing said solution to stand until said crystallization is complete and separating off said crystals.

11. The process as defined in claim 10, further comprising the steps of redissolving said crystals in a solution containing effective reductant and buffered to a pH between about 7.5 and 8.5, adjusting the pH to about 7.0 and cooling said solution to between $0°$ C and $10°$ C to crystallize out said hemoglobin in purified form.

12. Method as defined in claim 1, wherein the hemoglobin in said aqueous hemoglobin solution is a component of the blood of a living creature, said living creature being of a type which utilizes ferrous hemoglobin for the transport of oxygen.

13. Method as defined in claim 12, wherein said blood is collected in an anti-coagulant, red cells therein are separated by centrifugation, the red cells are washed with a solution containing about 0.85% sodium chloride, the red cells are lysed, and red cell ghosts are separated off by centrifugation.

14. Method as defined in claim 12, wherein said blood is defibrinated, the red cells are separated by centrifugation, the red cells are washed with a solution containing about 0.85% sodium chloride, the red cells are lysed, and the red cell ghosts are separated off by centrifugation.

15. Method as defined in claim 13, wherein said lysing is effected by suspending said red cells in distilled water.

16. The product comprising amorphous hemoglobin, buffer, and reductant produced by the method of claim 7.

17. A product comprising crystalline hemoglobin, buffer and reductant produced by the method of claim 8.

18. The process as defined in claim 8 wherein the pH of said solution is maintained at an acid pH at least as high as 6.0 during said crystallization step with the objective of obtaining hemoglobin suitable for absorption of negatively charged organic volatiles in addition to CO.

19. The process as defined in claim 8 wherein the pH is maintained at an alkaline pH with 8.5 as the upper limit during said crystallization step with the objective of obtaining hemoglobin suitable for absorption of positively charged volatiles in addition to CO.

20. A product comprising crystalline hemoglobin made by the method of claim 18.

21. A product comprising crystalline hemoglobin made by the method of claim 19.

* * * * *